United States Patent [19]

Bartholomew et al.

[11] Patent Number: 4,995,864
[45] Date of Patent: Feb. 26, 1991

[54] DUAL CHAMBER PUMPING APPARATUS

[75] Inventors: Victor L. Bartholomew, Escondido; Giorgio di Palma, Ramona, both of Calif.

[73] Assignee: Imed Corporation, San Diego, Calif.

[21] Appl. No.: 394,076

[22] Filed: Aug. 15, 1989

[51] Int. Cl.⁵ .............................................. A61M 1/00
[52] U.S. Cl. ....................................... 604/153; 604/9; 604/246; 417/480
[58] Field of Search ............................ 604/9, 131–132, 604/151, 153, 183, 185, 246–249; 417/478, 480

[56] References Cited

U.S. PATENT DOCUMENTS

| | | |
|---|---|---|
| 224,370 | 2/1880 | Wilson . |
| 493,208 | 3/1893 | Cruickshank . |
| 963,626 | 7/1910 | McCarty . |
| 1,223,963 | 4/1917 | Gollomb . |
| 2,449,573 | 9/1948 | White ................................ 277/60 |
| 3,085,549 | 4/1963 | Kacsuta ............................ 118/317 |
| 3,416,567 | 12/1968 | Dardel et al. .................... 137/604 |
| 3,595,240 | 7/1971 | Mishler ............................. 604/9 |
| 3,822,720 | 7/1974 | Souza ............................... 137/525.1 |
| 4,489,750 | 12/1984 | Nehring .......................... 137/496 |
| 4,850,955 | 7/1989 | Newkirk .......................... 604/9 |

Primary Examiner—Stephen C. Pellegrino
Assistant Examiner—Corrine Maglione
Attorney, Agent, or Firm—Neil K. Nydegger

[57] ABSTRACT

A dual chamber pumping apparatus and method for infusing fluids to a patient includes a disk having a fluid inlet and a fluid outlet. Resilient membranes are attached to opposite sides of the disk to establish dual pumping chambers, and a network of one-way valves connects the fluid inlet in alternating fluid communication with the pumping chambers. A one-way outlet valve connects the pumping chambers alternately in fluid communication with the fluid outlet. The one-way valves utilize a hollow, elastomeric tube fixedly disposed in passageways within the disk for covering and uncovering respective ports in response to fluid pressure differentials on the inner and outer surfaces of the walls of the hollow, elastomeric tube.

11 Claims, 1 Drawing Sheet

DUAL CHAMBER PUMPING APPARATUS

FIELD OF THE INVENTION

This invention relates generally to apparatus for pumping fluids. More specifically, the invention relates to a method and apparatus for pumping fluids utilizing dual pumping chambers. The present invention is particularly, though not exclusively, useful for being included in a system for infusing fluids to a patient in a medical environment.

BACKGROUND OF THE INVENTION

In the past, various devices for pumping fluids have been known and various types of apparatus have been utilized. A number of devices over the years have utilized dual pumping chambers to pump fluids therethrough. However, such devices have involved complicated piping and tubing structure utilizing complicated check valves. In addition, there are pumps which utilize flexible bulbs and the like for pumping but they do not effectively prevent the return flow of fluid during the pumping operation. In addition, some dual chamber pumping devices are specifically designed for sending the flow of fluid in a first direction, and sucking unwanted fluid back through the second chamber in a second direction, utilizing various check valves and neck valves to accomplish same. Such devices, however, are not practical in their use in that such flexible membrane type pumps are not well suited for allowing flow in a forward direction and preventing flow in a reverse direction in a manner to maintain a desired constant forward flow at the outlet for the pumping apparatus.

In addition, many such prior art apparatus are not well suited to use in the medical environment in that they are not conveniently encased so as to prevent the introduction of unwanted bacteria and contaminants. In addition, such prior art devices are not integrally formed with a minimal likelihood of moving parts becoming obstructed or failing to operate in a satisfactory manner. In addition, such pumping apparatus are not portable and easy and convenient to use, especially in a hospital or other medical environment. Moreover, such prior art devices are not durable in construction because of the complexity in machining complicated moving parts and elements of such assemblies involved. In addition, such prior art devices are not of a construction which is relatively easy to manufacture and assemble.

Accordingly, it is an object of the present invention to provide a dual chamber pumping apparatus which is reliable in operation. It is another object of the present invention to provide a pumping apparatus having a minimum of moving parts and which is constructed in a manner to provide increased durability. It is a further object of the present invention to provide a dual chamber pumping apparatus which is self-contained, portable and well suited for use in a hospital or other medical environment. A further object of the present invention is to provide a dual chamber pumping apparatus which is relatively easy and cost effective to manufacture and assemble, and which is convenient and easy to use.

SUMMARY OF THE INVENTION

A preferred embodiment of the dual chamber pumping apparatus for infusing fluids to a patient comprises a disk having a fluid inlet and a fluid outlet, and first and second resilient membranes attached to opposite sides of the disk to establish first and second pumping chambers. A first one-way valve connects the fluid inlet in fluid communication with the first pumping chamber, and a second one-way valve connects the fluid inlet in fluid communication with the second pumping chamber. The apparatus also has a one-way outlet valve for connecting the fluid outlet in alternating fluid communication with the first and second pumping chambers. In a preferred embodiment, each of the one-way valves comprises a hollow elastomeric tube disposed in an appropriate fluid passageway of the disk. Each tube is disposed in its passageway for covering and uncovering a port in the passageway in response to fluid pressure differentials on the inner and outer surfaces of the wall of the hollow elastomeric tube. Deformation of the first resilient membrane closes the first one-way valve and simultaneously opens the one-way outlet valve for allowing fluid to flow from the first pumping chamber out the fluid outlet, while allowing the second chamber to be filled with fluid from the fluid inlet. Deformation of the second resilient membrane closes the second one-way valve and simultaneously opens the one-way outlet valve for allowing fluid to flow from the second pumping chamber out the fluid outlet, while allowing the first chamber to again be filled with fluid from the fluid inlet.

The novel features of this invention, as well as the invention itself, both as to its structure and its operation, will be best understood from the accompanying drawings, taken in conjunction with the accompanying description, in which similar reference characters refer to similar parts, and in which:

DETAILED DESCRIPTION OF THE PREFERRED EMBODIMENT

Figure 1:
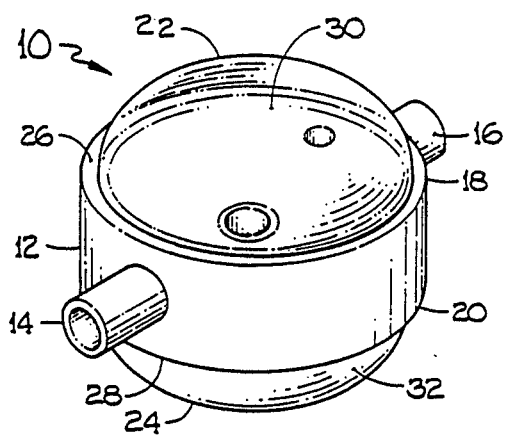
FIG. 1 is a perspective view of a preferred embodiment of the dual chamber pumping apparatus in accordance with the present invention.

FIG. 1 shows the dual chamber pumping apparatus of the present invention generally designated as 10. The dual chamber pumping apparatus 10 comprises a disk 12 having a fluid inlet 14 and a fluid outlet 16. The disk 12 functions as the body for the device within which the passageways for the fluid and various valve mechanisms are contained, as will be more fully explained below. The disk 12 has a cylindrical shape and has a first side 18 and a second, opposite side 20. First and second resilient membranes 22 and 24, respectively, are sealed about their respective edges along a top rim 26 and a bottom rim 28, to establish a first pumping chamber 30 and a second pumping chamber 32. The membrane may advantageously be transparent to allow observation of the interior of the apparatus 10.

Figure 2:
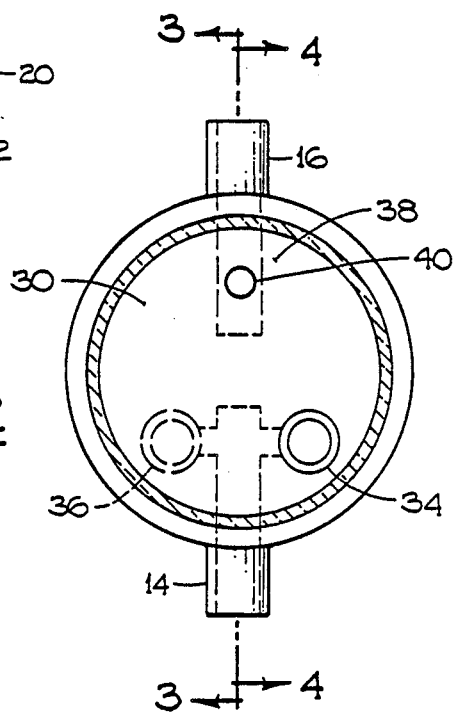
FIG. 2 is a top view of the dual chamber pumping apparatus shown in FIG. 1.

As can be further appreciated with reference to FIG. 2, the fluid inlet 14 is connected with the first pumping chamber 30 via a first one-way valve 34. Fluid inlet 14 is also connected to second pumping chamber 32 by second one-way valve 36 shown in dotted lines in FIG. 2. As further shown in FIG. 2, the disk 12 includes fluid outlet 16 connected in fluid communication with first and second pumping chambers 30 and 32 by a one-way outlet valve 38. Operation of the one-way valves 34, 36 and 38 is illustrated with further reference to FIGS. 3 and 4.

In particular, operation of the one-way valves can perhaps best be appreciated by further description of one-way outlet valve 38. In particular, it includes a first outlet port 40 in fluid communication with first pumping chamber 30. One end of outlet port 40 abuts against an outer wall 42 of a section of hollow resilient tube 44, preferably a hollow elastomeric tube, which is disposed in passageway 46 of fluid outlet 16. One end 48 of tube 44 is fixedly connected within passageway 46, and the opposite end is freely movable between an open position and a closed position with respect to the first outlet port 40 for covering and uncovering the port 40 in response to fluid pressure differentials on the inner surface 50 and outer surface 42 of the wall of tube 44. First one-way valve 34 likewise comprises a tube 52 aligned in a passageway 54 having a first inlet port 56 opening against the outer wall of tube 52. Second one-way valve 36 likewise has a tube 58 in a passageway 60 having a second inlet port 62 connected in fluid communication between the lumen 64 of fluid inlet 14 and the second pumping chamber 32. First one-way valve 36 likewise establishes fluid communication between lumen 64 of inlet port 14 with first pumping chamber 30.

Figure 3:
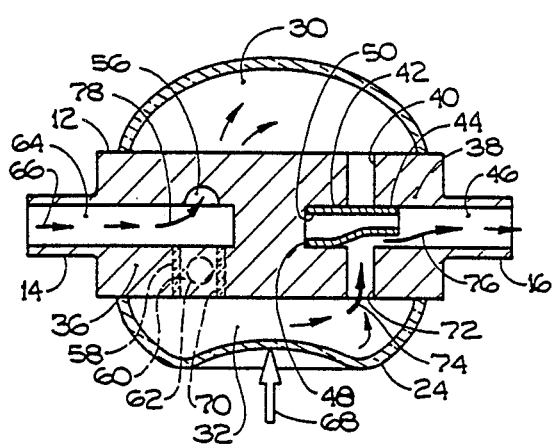
FIG. 3 is a side cross-sectional view taken along line 3—3 of the dual chamber pumping apparatus schematically illustrating one phase of the operation thereof.

In operation, fluid is introduced into fluid inlet 14 and has a fluid flow path as indicated by arrows 66. The incoming fluid at inlet 14 is under a pressure sufficient to collapse tubes 52, 58 to open first and second one-way valves 34, 36 so fluid enters pumping chambers 30, 32. The fluid pressure is insufficient, however, to collapse tube 44, so one-way outlet valve 38 remains closed, thereby allowing pumping chambers 30, 32 to be filled. As shown in FIG. 3, a force is then applied as indicated by arrow 68 on second pumping chamber 32. This deforms the resilient membrane 24, thereby increasing the fluid pressure within pumping chamber 32 to be greater than that of the incoming fluid pressure at inlet 14, so as to hold the fluid under pressure within passageway 60. This exerts pressure on the inner wall 70 of tube 58, so as to prevent a back flow of fluid from second pumping chamber 32 into the fluid inlet lumen 64. The fluid pressure increase within second pumping chamber 32 caused by force 68 simultaneously forces the fluid out through second outlet port 72 as shown by arrows 74. This allows the elastomeric resilient tube 44 to be partially collapsed to uncover second outlet port 72, thereby allowing fluid to flow into passageway 46 as indicated by arrow 76. In addition, the increased pressure of the fluid within passageway 46 exerts fluid pressure on the inner surface 50 of the wall of tube 44 so as to prevent fluid from moving into first port 40, for covering the end of first port 40. This prevents fluid from moving from first pumping chamber 30 into passageway 46 of the fluid outlet 16.

Figure 4:
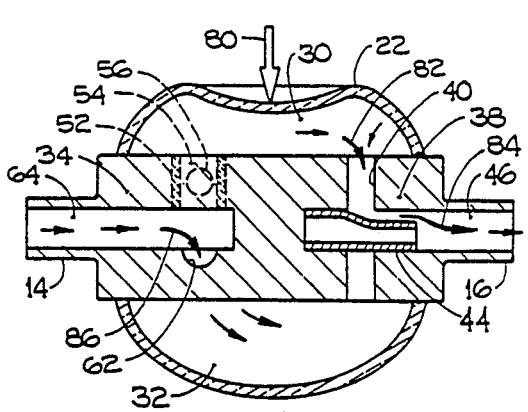
FIG. 4 is a cross-sectional side view taken along line 4—4 of the dual chamber pumping apparatus shown in FIG. 2 in an alternate phase of operation in accordance with the present invention.

At the same time that the force 68 has been applied to second membrane 24, so as to pump fluid out through the one-way outlet valve 38 via second outlet port 72, fluid has been introduced as shown by flow arrow 66 into the lumen 64 of fluid inlet 14. The fluid is prevented, however, from flowing back into second pumping chamber 32 by the action of second one-way valve 36, as explained above, so that the fluid can only flow into first pumping chamber 30 via first inlet port 56 as shown by arrow 78, for filling the first pumping chamber 30. After the first pumping chamber 30 has been filled, an alternate force 80 as shown in FIG. 4 by arrow 80 is applied to first membrane 22. This causes a mirror image operation of that discussed with respect to FIG. 3. In other words, one-way valve 34 is held in its closed position so as to cover inlet port 56 and block flow of fluid out of first pumping chamber 30 into the fluid inlet 14, and directs flow of fluid as shown by arrows 82 into first outlet port 40, uncovering port 40 by the action of the tube 44. This allows the fluid to flow into passageway 46 of fluid outlet 16 as indicated by arrow 84. Likewise, additional incoming fluid into fluid inlet 14 is directed as shown by arrow 86 through second inlet port 62 into pumping chamber 32 for again filling second pumping chamber 32.

Thus, it can be seen by alternating forces 68, 80 for alternating deformation of the resilient membranes 22 and 24, an efficient pumping action can be generated for moving fluid into fluid inlet 14 and out of fluid outlet 16. There are a minimum of moving parts, yet the invention provides a durable and reliable method and apparatus for infusing fluid in a simple and efficient manner to a patient.

While the particular dual chamber pumping apparatus as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

What is claimed is:

1. A dual chamber pumping apparatus for use in infusing fluids to a patient, comprising:
   a disk having a fluid inlet and a fluid outlet;
   a first resilient membrane attached to said disk to establish a first pumping chamber, and a second resilient membrane attached to said disk to establish a second pumping chamber;
   a first one-way valve for connecting said fluid inlet in fluid communication with said first pumping chamber, and a second one-way valve for connecting said fluid inlet in fluid communication with said second pumping chamber; and
   a one-way outlet valve for connecting said fluid outlet in alternating fluid communication with said first and second pumping chambers.

2. A dual chamber pumping apparatus for use in infusing fluids to a patient as recited in claim 1, wherein said first one-way valve is movable between an open position for allowing fluid flow from said fluid inlet into said first pumping chamber, and a closed position for preventing fluid flow from said first pumping chamber into said fluid inlet.

3. A dual chamber pumping apparatus for use in infusing fluids to a patient as recited in claim 2, wherein said second one-way valve is movable between an open position for allowing fluid from said fluid inlet into said second pumping chamber, and a closed position for preventing fluid flow from said second pumping chamber into said fluid inlet.

4. A dual chamber pumping apparatus for use in infusing fluids to a patient as recited in claim 3, wherein said one-way outlet valve is movable between an open position for alternately allowing fluid flow from only one of said first and second pumping chambers to said fluid outlet, and a closed position for preventing fluid flow from said fluid outlet back into said first and second pumping chambers.

5. A dual chamber pumping apparatus for use in infusing fluids to a patient as recited in claim 4 further comprising means for supplying a fluid to said fluid inlet for filling said first pumping chamber, and wherein deformation of said first resilient membrane closes said first one-way valve and simultaneously opens said one-way outlet valve for allowing fluid to flow from said first pumping chamber out said fluid outlet, while allowing said second chamber to be filled with fluid from said fluid inlet.

6. A dual chamber pumping apparatus for use in infusing fluids to a patient as recited in claim 5, wherein deformation of said second resilient membrane closes said second one-way valve and simultaneously opens said one-way outlet valve for allowing fluid to flow from said second pumping chamber out said fluid outlet, while allowing said first chamber to be filled with fluid from said fluid inlet.

7. A dual chamber pumping apparatus for use in infusing fluids to a patient as recited in claim 1, wherein said first and second one-way valves each comprise said disk having a fluid passageway, and a hollow elastomeric tube fixedly disposed in said passageway, each tube having a first end secured to said passageway to block fluid flow and a second end resiliently disposed in said passageway operable between an open position for allowing fluid flow in a forward direction and a closed position for preventing fluid flow in a reverse direction.

8. A dual chamber pumping apparatus for use in infusing fluids to a patient as recited in claim 7, wherein said one-way outlet valve comprises said disk having a fluid passageway, and a hollow elastomeric tube positioned therein, having one end secured in said passageway for blocking fluid flow, and a second end resiliently disposed in said passageway movable between an open position for alternately allowing fluid flow from only one of said first and second pumping chambers to said fluid outlet, and a closed position for preventing fluid flow from said fluid outlet back into said first and second pumping chambers.

9. A dual chamber pumping apparatus for use in infusing fluids to a patient comprising:
a disk having a fluid inlet and a fluid outlet; and
a first resilient membrane attached to a first side of said disk for establishing a first pumping chamber, and a second resilient membrane attached to a second side of said disk for establishing a second pumping chamber;
said disk having inlet valve means for connecting said fluid inlet in fluid communication with said first pumping chamber and said second pumping chamber, said valve means including a first one-way valve movable between an open position for allowing fluid to flow from said fluid inlet into said first pumping chamber and a closed position for preventing fluid from flowing from said first pumping chamber back into said fluid inlet, said valve means further including a second one-way valve movable between an open position for allowing fluid to flow from said fluid inlet into said second pumping chamber and a closed position for preventing fluid from flowing from said first pumping chamber back into said fluid inlet;
said disk further having outlet valve means connecting said first and second pumping chambers in fluid communication with said fluid outlet, said outlet valve means including a one-way outlet valve for preventing fluid flow from said fluid outlet back into said first and second pumping chambers, and being movable between a first position for allowing fluid to flow from said first pumping chamber into said fluid outlet while preventing fluid from flowing from said second pumping chamber into said fluid outlet, and a second position for allowing fluid to flow from said second pumping chamber into said fluid outlet while preventing fluid from flowing from said first pumping chamber into said fluid outlet.

10. A dual chamber pumping apparatus for use in infusing fluids to a patient as recited in claim 9, wherein said inlet valve means and outlet valve means each comprise said disk having a generally cylindrical bore having a port in the wall thereof, and a hollow elastomeric tube fixedly disposed in said bore for covering and uncovering said port in response to fluid pressure differentials on the inner and outer surface of the wall of said hollow tube.

11. A method of pumping fluid to a patient comprising:
providing a disk having a fluid inlet and a fluid outlet;
attaching a first resilient membrane to said disk to establish a first pumping chamber, and a second resilient membrane to an opposite side of said disk to establish a second pumping chamber;
providing a first one-way valve for connecting said fluid inlet in fluid communication with said first pumping chamber, and providing a second one-way valve for connecting said fluid inlet in fluid communication with said second pumping chamber;
providing a one-way outlet valve for connecting said fluid outlet in alternating fluid communication with said first and second pumping chambers;
deforming said first resilient membrane to close said first one-way valve and simultaneously open said one-way outlet valve for allowing fluid to flow from said first pumping chamber out said fluid outlet while allowing said second chamber to be filled with fluid from said fluid inlet; and
subsequently deforming said second resilient membrane to close said second one-way valve and simultaneously open said one-way outlet valve for allowing fluid to flow from said second pumping chamber out said fluid outlet while allowing said first chamber to be filled with fluid from said fluid inlet.

* * * * *